(12) United States Patent
Ikushima et al.

(10) Patent No.: US 9,719,896 B2
(45) Date of Patent: Aug. 1, 2017

(54) AID FOR FILLING LIQUID, AND METHOD FOR FILLING LIQUID

(71) Applicants: MUSASHI ENGINEERING, INC., Mitaka-shi, Tokyo (JP); NICHIREI BIOSCIENCES INC., Tokyo (JP)

(72) Inventors: Naotoshi Ikushima, Mitaka (JP); Toshiyuki Kasamatsu, Higashimurayama (JP); Ryohei Suzuki, Higashimurayama (JP)

(73) Assignees: MUSASHI ENGINEERING, INC., Tokyo (JP); NICHIREI BIOSCIENCES, INC., Tokyo (JP)

( * ) Notice: Subject to any disclaimer, the term of this patent is extended or adjusted under 35 U.S.C. 154(b) by 0 days.

(21) Appl. No.: 14/759,612

(22) PCT Filed: Jan. 8, 2014

(86) PCT No.: PCT/JP2014/050100
§ 371 (c)(1),
(2) Date: Jul. 7, 2015

(87) PCT Pub. No.: WO2014/109323
PCT Pub. Date: Jul. 17, 2014

(65) Prior Publication Data
US 2016/0003718 A1    Jan. 7, 2016

(30) Foreign Application Priority Data
Jan. 8, 2013   (JP) .................................. 2013-001023

(51) Int. Cl.
*A61B 10/00*   (2006.01)
*G01N 1/31*    (2006.01)
(Continued)

(52) U.S. Cl.
CPC ................. *G01N 1/312* (2013.01); *B01L 3/52* (2013.01); *B01L 9/52* (2013.01); *B01L 9/527* (2013.01);
(Continued)

(58) Field of Classification Search
CPC ................................. G01N 1/312; G01N 1/30
See application file for complete search history.

(56) References Cited

U.S. PATENT DOCUMENTS

| | | | |
|---|---|---|---|
| 4,392,450 A | 7/1983 | Prevo | |
| 4,985,206 A | 1/1991 | Bowman et al. | |

(Continued)

FOREIGN PATENT DOCUMENTS

| | | |
|---|---|---|
| EP | 0310399 A2 | 4/1989 |
| JP | 5-14891 U | 2/1993 |

(Continued)

OTHER PUBLICATIONS

International Search Report dated Mar. 11, 2014, issued in corresponding application No. PCT/JP2014/050100 (2 pages).

*Primary Examiner* — Jyoti Nagpaul
(74) *Attorney, Agent, or Firm* — Westerman, Hattori, Daniels & Adrian, LLP

(57) ABSTRACT

A liquid filling aid that is placed on a plate-shaped member and defines a reaction chamber to be filled with a liquid, the aid includes a main body, a storage section that is formed in the main body and stores the liquid, a reaction section that is a recess formed at a bottom of the main body, a communication aperture for fluid communication between the storage section and the reaction section, and an air vent for communication between the reaction section and outside air, wherein the reaction section and an upper surface of the plate-shaped member define the reaction chamber and a liquid filling method including a step of placing the liquid
(Continued)

filling aid on the plate-shaped member, and a step of discharging the liquid in an amount equal to or larger than the volume of the reaction chamber for supply to the storage section.

18 Claims, 9 Drawing Sheets

(51) Int. Cl.
  *G01N 1/30*  (2006.01)
  *G01N 35/10*  (2006.01)
  *B01L 3/00*  (2006.01)
  *B01L 9/00*  (2006.01)

(52) U.S. Cl.
  CPC ........... *G01N 1/30* (2013.01); *G01N 35/1002* (2013.01); *B01L 2200/025* (2013.01); *B01L 2200/026* (2013.01); *B01L 2200/027* (2013.01); *B01L 2200/0621* (2013.01); *B01L 2200/0684* (2013.01); *B01L 2300/047* (2013.01); *B01L 2300/048* (2013.01); *B01L 2300/0822* (2013.01); *B01L 2300/0877* (2013.01); *B01L 2400/0406* (2013.01)

(56) References Cited

U.S. PATENT DOCUMENTS

| | | |
|---|---|---|
| 5,922,604 A | 7/1999 | Stapleton et al. |
| 6,218,191 B1 | 4/2001 | Palander |
| 6,673,620 B1 * | 1/2004 | Loeffler .................. B01L 3/502 |
| | | 359/398 |
| 2005/0186114 A1 | 8/2005 | Reinhardt et al. |
| 2005/0233367 A1 | 10/2005 | Chu |
| 2005/0270642 A1 | 12/2005 | McLellan et al. |
| 2009/0286305 A1 | 11/2009 | Chu |
| 2010/0002293 A1 | 1/2010 | McLellan et al. |
| 2013/0078734 A1 | 3/2013 | McLellan et al. |

FOREIGN PATENT DOCUMENTS

| | | |
|---|---|---|
| JP | 2000-508423 A | 7/2000 |
| JP | 2002-350305 A | 12/2002 |
| JP | 2005-530208 A | 10/2005 |
| JP | 2007-532918 A | 11/2007 |

* cited by examiner (a)

(b)

(a)

(b)

AID FOR FILLING LIQUID, AND METHOD FOR FILLING LIQUID

TECHNICAL FIELD

The present invention relates to a liquid filling aid and a liquid filling method. More particularly, the present invention relates to a liquid filling aid used, for example, in a step of staining a biological tissue, a cell, or the like, which is adhered or attached onto a slide glass, and further relates to a liquid filling method using the liquid filling aid.

BACKGROUND ART

The immunohistochemical staining method is to clarify the local existence (localized position) of a substance, which exists inside a tissue cell and has antigenicity, by utilizing a specific immune reaction called an antigen-antibody reaction.

Operations for the immunohistochemical staining are generally performed through a plurality of steps as follows. A first step is a deparaffinization step of dissolving paraffin embedding a specimen, which has been attached onto a slide glass and immobilized using a formalin solution, etc., with an organic solvent. A second step is a hydrophilization step of removing the organic solvent to increase affinity of the specimen to water. A third step is an antigen retrieval step of performing treatment to increase immuno-reactivity. A fourth step is a primary antibody applying step of applying an antibody that reacts with the antigen in the specimen. A fifth step is a detection step of applying a reagent to detect the antibody having reacted. A sixth step is a color developing step of applying a reagent to visualize the detection reagent. A seventh step is a staining of nuclei with a different color to confirm the morphology feature of tissues easily.

Various apparatuses for carrying out general staining processes, including the above-described immunohistochemical staining process, have been proposed so far. In those apparatuses, a cover placed on a slide glass serves to fill or hold a reagent, etc. For example, Patent Document 1 discloses a cover for a base comprising a main body that is positioned above a base, and that defines a cavity to form a reaction chamber, and a projected portion that projects from the main body, and that defines a fluid container in fluid communication with the cavity when the cover is mounted to the base.

Patent Document 2 discloses an apparatus for treating a human or animal cell sample with a treatment liquid, the apparatus comprising means for applying the treatment liquid to a surface of a slide on which the sample is held, and means for determining a contour of the sample with setting a cover tile, which has a recessed surface, on a slide, wherein the apparatus further comprises means for applying a sealing liquid to a joined boundary between the slide and the cover tile from the outside of a cavity, thereby sealing off a gap generated between the cover tile and the slide.

Patent Document 3 discloses an apparatus for extracting biological molecules from a tissue specimen, the apparatus comprising a base having an upper surface and a bottom surface, the base holding the tissue specimen on the upper surface of the base, a slide cover placed on the upper surface of the base and having an inner surface, the upper surface of the base and the inner surface of the slide cover forming a space to hold an extraction buffer solution, and a temperature controller connected to the bottom surface of the base. Patent Document 3 further discloses the following features. The inner surface of the slide cover projects toward the base in a central portion the slide cover, whereby the space formed by the upper surface of the base and the inner surface of the slide cover is shallowed around a central portion (Claim 3). The slide cover has an opening formed in the central portion to allow the extraction buffer solution to be added into the space between the upper surface of the base and the inner surface of the slide cover (Claim 15). The slide cover further includes at least one outer surface hole in a peripheral portion thereof (Claim 16).

CITATION LIST

Patent Documents

Patent Document 1: Japanese National Publication of International Patent Application No. 2005-530208
Patent Document 2: Japanese National Publication of International Patent Application No. 2000-508423
Patent Document 3: Japanese National Publication of International Patent Application No. 2007-532918

SUMMARY OF INVENTION

Technical Problem

However, the covers of the types disclosed in Patent Documents 1 and 2 have the following problems.

(1) There is a risk that, when the liquid is filled over a comparatively long distance from one short-side located end of the cover to the other short-side located end (i.e., substantially over the entire length of the slide cover in a longitudinal direction), the filling may be insufficient when only a force due to the capillary action is utilized for the filling. Therefore, an additional mechanism aiding the filling is required which operates, for example, to slide the cover, or to suck the liquid from the side opposite to the side where the liquid is discharged for supply. In the configuration disclosed in Patent Document 3, the space defined by the cover and the base cannot be fully filled with the liquid only by the capillary action for its specific nature.

(2) Because the cover is widely opened at the end along the short side, drying tends to occur due to evaporation of the liquid therethrough. The drying may cause a risk that nonspecific staining not attributable to the antigen-antibody reaction generates in a dried portion. This raises a problem of necessitating additional filling of the liquid until the reaction progresses sufficiently.

(3) In the method of developing the reaction under heating, because evaporation of the liquid is promoted and drying is accelerated, there is a risk that insufficient reaction or uneven staining may occur. This also raises the problem of necessitating additional filling of the liquid until the reaction progresses sufficiently.

However, adding the liquid at a lower temperature (namely, mixing a liquid having been already heated and a liquid to be heated) reduces the temperature of the reaction phase. Thus, a sufficient amount of heat cannot be applied to the tissue. Such a situation causes a possibility that uneven staining or insufficient staining may occur, and is not preferable for the reaction. Accordingly, temperature control (temperature conditioning) of the liquid is needed.

(4) When bubbles are mixed into the liquid filled in the cover, the cover has to be, for example, relatively moved to remove the bubbles.

(5) Because the liquid has to be discharged toward a narrow range, e.g., an end portion of the cover, accurate positioning of a discharge port is needed.

An object of the present invention is to provide a liquid filling aid and a liquid filling method, which are able to solve the problems described above.

Solution to Problem

According to a first invention, there is provided a liquid filling aid that is placed on a plate-shaped member and defines a reaction chamber to be filled with a liquid, the aid comprising a main body (30), a storage section (2) that is formed in the main body and stores the liquid, a reaction section (8) that is a recess formed at a bottom of the main body, a communication aperture (15) for fluid communication between the storage section and the reaction section, and an air vent (14) for communication between the reaction section and outside air, wherein the reaction section and an upper surface of the plate-shaped member define the reaction chamber (17).

According to a second invention, in the first invention, the storage section (2) has a larger volume than that of the reaction section (8).

According to a third invention, in the first invention, the storage section (2) is arranged above the reaction section (8) with the communication aperture interposed therebetween.

According to a fourth invention, in the third invention, an opening (3) of the storage section is formed in an upper surface of the main body (30). Here, the communication aperture (15) may be positioned substantially at a center of the reaction section (8).

According to a fifth invention, in the first invention, the air vent (14) penetrates from an upper surface of the reaction section (8) up to an upper surface of the main body (30).

According to a sixth invention, in the first invention, the reaction section (8) is constituted with a depth at which a force due to capillary action is generated over an entire region of the reaction section.

According to a seventh invention, in the sixth invention, the depth of the reaction section is 10 to 200 μm.

According to an eighth invention, in the first invention, a bottom of the storage section (2) has a slope or a groove extending toward the communication aperture.

According to a ninth invention, in the first invention, at least one slope extending toward the communication aperture (15) has two or more gradients.

According to a tenth invention, in the first invention, the storage section (2) includes a first recess (24) in which the communication aperture is provided substantially at a center, and a second recess that is positioned above the first recess, and that has a volume twice or more as much as that of the first recess.

According to an eleventh invention, in the first invention, an inner upper (ceiling) surface of the reaction section (8) has a slope or a groove extending toward the air vent, and the air vent (14) is disposed at a highest position of the inner upper surface of the reaction section.

According to a twelfth invention, in any one of the first to eleventh inventions, the main body (30) is made of a metal material.

According to a thirteenth invention, in any one of the first to eleventh inventions, the plate-shaped member is a slide glass used in a staining step.

According to a fourteenth invention, there is provided an automatic staining apparatus comprising a liquid discharge device, a palette that holds a slide glass, a driving device that moves the discharge device in XYZ directions relative to the palette, a holder that holds the liquid filling aid according to the eleventh invention, and an elevating/lowering device that moves the holder up and down. Here, the automatic staining apparatus may further comprise a stage with a heating function, and a resilient member that biases the palette upward. The palette may have an opening that allows the stage to pass through the opening when the resilient member is contracted.

According to a fifteenth invention, there is provided a liquid filling method using the liquid filling aid according to any one of the first to eleventh inventions, the method comprising a step of placing the liquid filling aid on the plate-shaped member, and a step of discharging the liquid in an amount equal to or larger than the volume of the reaction chamber to the storage section.

Advantageous Effects of Invention

The following advantageous effects are obtained with the present invention.

(1) Since the liquid filling aid of the present invention includes the communication aperture for communication between the reaction section and the storage section, the liquid can be filled to every corners of the reaction section only by a force generated due to the capillary action. Furthermore, since the liquid stored in the storage section is caused to flow down into the reaction section through the communication aperture under the weight of the liquid itself, an additional mechanism for aiding the filling is not needed.

(2) When the liquid filling aid of the present invention is placed on the slide glass, the reaction section constitutes the reaction chamber that is a closed space. Therefore, drying can be avoided. Moreover, by filling the liquid in the reaction section until the liquid reaches the air vent, a contact area between the liquid and air can be reduced, and the drying can be delayed.

(3) Since the liquid filling aid of the present invention includes the storage section for storing the liquid, the problem with evaporation of the liquid can be dealt with. Furthermore, since the storage section for storing the liquid is disposed adjacent to the reaction section, the liquid stored in the storage section can be heated at the same time as heating for the reaction.

(4) Since the liquid filling aid of the present invention includes the air bent in communication with the reaction section, bubbles are released through the air bent even when the bubbles are mixed into the liquid.

(5) In the configuration where the top of the storage section is widely opened, accurate positioning of the ejection port is not required.

BRIEF DESCRIPTION OF THE DRAWINGS

FIG. 4(a) represents a state immediately after the liquid has been discharged toward a storage section, FIG. 4(b) represents a state where the liquid flows into a reaction section from the storage section through a communication aperture, and FIG. 4(c) represents a state where the liquid has been filled in the entirety of the reaction section.

FIG. 6(a) represents a state before the liquid filling aid is placed, and FIG. 6(b) represents a state after the liquid filling aid has been placed.

DESCRIPTION OF EMBODIMENTS

An exemplary embodiment for carrying out the present invention will be described.

First Embodiment

Constitution

Figure 1:
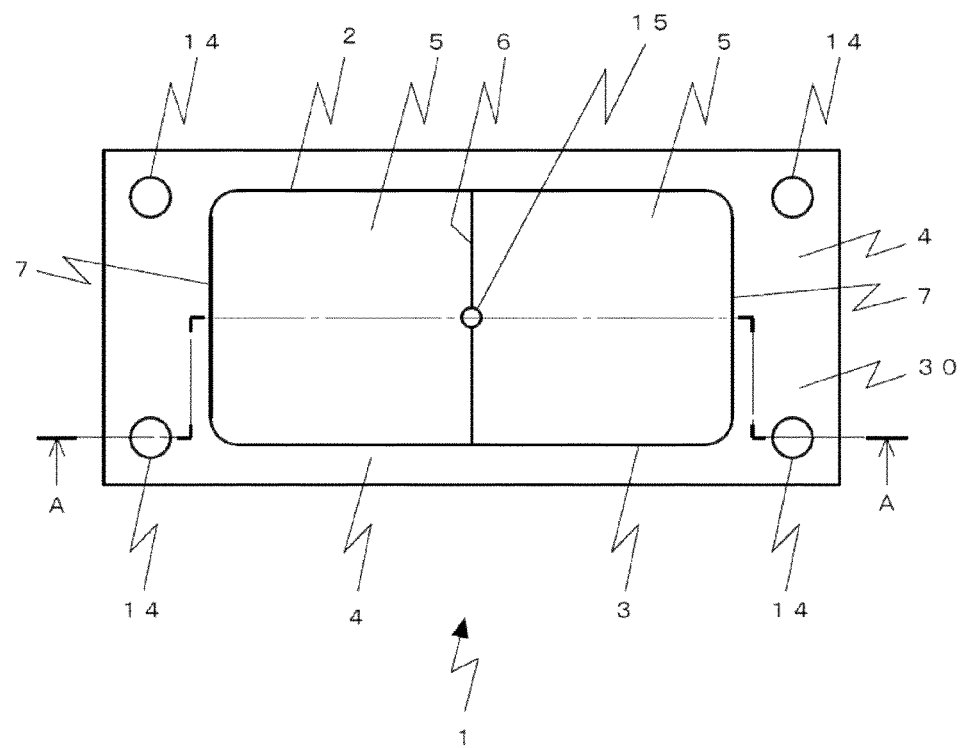
FIG. 1 is a plan view of a liquid filling aid according to a first embodiment.
Figure 2:
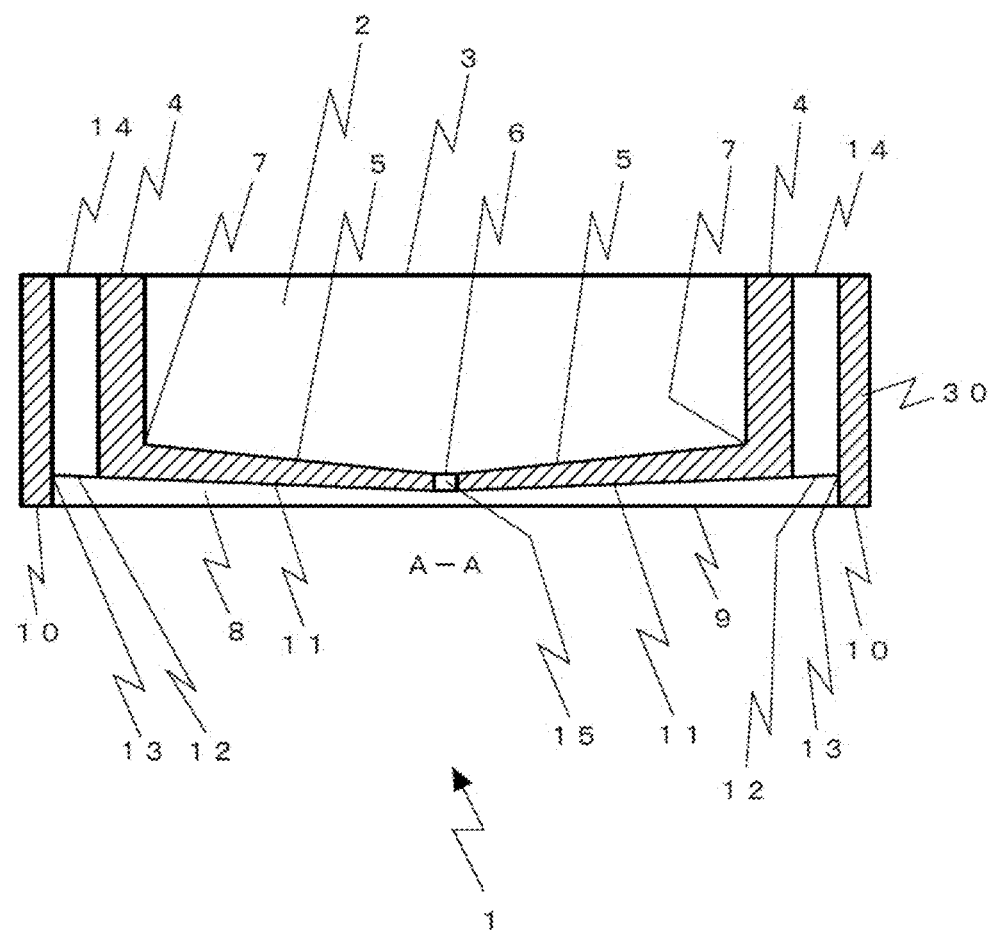
FIG. 2 is a sectional view taken along a line A-A in FIG. 1.
Figure 3:
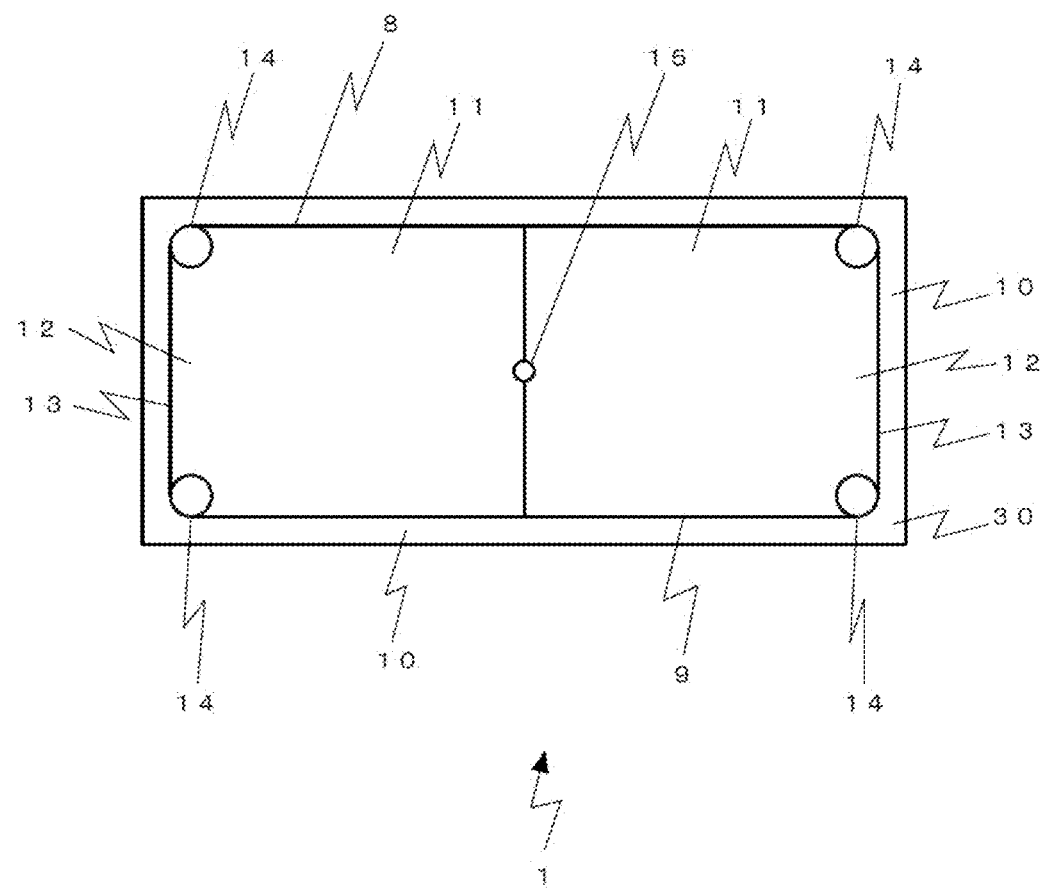
FIG. 3 is a bottom view of the liquid filling aid according to the first embodiment.

FIG. 1 is a plan view of a liquid filling aid 1 according to this embodiment, FIG. 2 is a sectional view taken along a line A-A in FIG. 1, and FIG. 3 is a bottom view of the liquid filling aid 1 according to the first embodiment. In the following description, the right and left direction in FIG. 1 or 3 is called a width direction, the up and down direction is called a lengthwise direction, and the up and down direction in FIG. 2 is called a height direction in some cases.

The liquid filling aid 1 according to this embodiment is constituted by forming, in a main body 30 made of a rectangular parallelepiped member, a storage section 2, a reaction section 8, an air vent 14, and a communication aperture 15. The liquid filling aid 1 is placed on a slide glass 16, described later, when it is used. The length of the liquid filling aid 1 in the lengthwise direction is equal to or slightly shorter than that of a short side of the slide glass 16. The length of the liquid filling aid 1 in the width direction is about ⅔ of that of a long side of the slide glass 16. Those lengths of the liquid filling aid 1 are changed as appropriate depending on the usable region of the slide glass 16. A remaining about ⅓ portion of the slide glass 16, the portion being not covered with the liquid filling aid 1, serves as a space for marking with identifiers such as characters, symbols, a barcode, or the like. The shape of the main body 30 is not limited to the illustrated rectangular parallelepiped, and the main body 30 may have a polygonal prismatic shape, a circular columnar shape, or an elliptic columnar shape. The individual components will be described in detail below.

The storage section 2 is in the form of a recess and is opened at its top to the upper surface side of the main body 30. The storage section 2 has a volume several to several-ten times (e.g., 60 times) as much as that of a reaction chamber 17. While the illustrated storage section 2 has a rectangular shape when viewed from above, the shape of the storage section 2 is not limited to the illustrated one. The shape of the storage section 2 when viewed from above may be polygonal, circular, or elliptic. The depth of the storage section 2 is preferably ½ or more and more preferably ⅔ or more of the height of the main body 30 (rectangular parallelepiped). The width and the length (area of an opening 3) of the storage section 2 is set to provide an area slightly smaller than that of an upper surface of the rectangular parallelepiped excepting a wall 4 that defines the storage section 2. In other words, the width and the length of the storage section 2 are set smaller than the width and the length (area of an opening 9) of the reaction section 8 by sizes corresponding to a space where the air vent 14 is disposed. Here, the volume of the storage section 2 determined from the depth, the width and the length is different depending on the amount of a liquid 19 required in a staining reaction. Thus, the volume of the storage section 2 is not limited to the above-mentioned example, and it may be changed on demand. However, the volume of the storage section 2 is preferably larger than that of the reaction section 8. The reason is that, by so setting the volume of the storage section 2, the liquid can be stored in the storage section 2 at a time in volume corresponding to both an amount necessary for filling the reaction section 8 and an amount additionally required later. A liquid, e.g., a solution for an antigen retrieval, a solution containing an antibody that reacts with the antigen, distilled water, or an organic solvent, is discharged from a discharge device 18 for supply to the storage section 2.

An inner lower surface of the storage section 2 is constituted by two slopes 5 and 5 that descend toward a center from two short sides 7 and 7 of the storage section 2, respectively. One communication aperture 15 is formed at a center of a lowermost portion 6 at which the two slopes 5 intersect. By providing the slopes 5 as described above, the liquid 19 stored in the storage section 2 can be forced to naturally flow toward the communication aperture 15. The number of the slopes 5 is not limited to two. As another example, the slopes may be formed by four surfaces like a quadrangular pyramid, and the communication aperture 15 may be provided at a position corresponding to the apex of the quadrangular pyramid. Alternatively, each slope may be constituted as a partly sloped surface like a groove. Thus, the slope may be of any desired type insofar as the liquid 19 stored in the storage section 2 is able to naturally flow toward the communication aperture 15 along the slope. The slope involves a bent surface or a groove-equipped bottom surface as well. The communication aperture 15 may be provided plural.

The reaction section 8 is in the form of a recess and is opened at its lower side at the bottom of the main body 30. When the liquid filling aid 1 is placed and fixed on the slide glass 16, the reaction section 8 constitutes a closed space (later-described reaction chamber 17). Here, the term "slide glass" means a glass plate on which a minute sample is placed mainly in the case of observing the sample with an optical microscope. In this embodiment, a slide glass having a common size with a short side of about 2.5 cm, a long side of about 7.5 cm, and a height of about 1.2 mm. While the illustrated reaction section 8 has a rectangular shape when viewed from below, the shape of the reaction section 8 is not limited to the illustrated one. The shape of the reaction section 8 when viewed from below may be polygonal, circular, or elliptic. However, the reaction section 8 preferably has a circular columnar space from the viewpoint of causing the liquid 19 to be evenly filled into the reaction section 8 with the capillary action. The depth of the reaction section 8 is basically determined depending on the amount of the liquid 19 necessary for the reaction, but it is preferably set to such a value as allowing a force due to the capillary action to act on the liquid 19 having flowed into the space (reaction chamber 17) defined by the reaction section 8 and the slide glass 16. For example, the depth of the reaction section 8 is preferably 10 to 200 μm and more preferably 10 to 100 μm. The width and the length (area of the opening 9)

of the reaction section 8 is set to provide an area slightly smaller than that of a lower surface of the rectangular parallelepiped excepting the thickness of a wall 10 that surrounds four sides of the reaction section 8. Similarly to the storage section 2, the volume of the reaction section 8 is also different depending on the amount of the liquid 19 required in the staining reaction. Thus, the volume of the reaction section 8 is not limited to the above-mentioned example, and it may be changed on demand.

An inner upper surface of the reaction section 8 is constituted by two slopes 11 and 11 that ascend from a center toward two short-side located ends 13 and 13 of the reaction section 8, respectively. The gradient of the slope is preferably set to such a value as allowing the liquid 19 to flow and reach the short-side located ends 13 and 13 from the center by a force generated due to the capillary action. The value of the gradient is preferably substantially $1/100$ and more preferably substantially $1/200$, for example. By providing the slopes 11 as described above, the liquid 19 can be filled into the reaction section 8 by the force generated due to the capillary action, and air in the reaction section 8 or bubbles mixed into the liquid 19 can be naturally moved along the slopes 11 toward the air vent 14 that are formed at the short-side located ends 13. Similarly to the slopes 5 of the storage section 2, the number of the slopes 11 is not limited to two. Thus, the slopes 11 may be formed by four surfaces, or each slope may be constituted as a partly sloped surface like a groove. Thus, the slope may be of any desired type insofar as air or bubbles are able to naturally move along the slope. The slope involves a bent surface or a groove-equipped bottom surface as well.

Since the reaction section 8 constitutes a closed space (reaction chamber 17) when the liquid filling aid 1 is placed on and fixed to the slide glass 16, drying due to evaporation of the liquid 19 is less likely to occur. On the other hand, even when the amount of the liquid 19 supplied to the storage section 2 is larger than the volume of the reaction section 8, the liquid 19 is less likely to leak out (namely, the liquid can be held at least for a time required for the reaction) because the reaction section 8 is closed. A sealing member, a packing, or the like may be disposed under the rectangular wall 10.

At a highest position 12 of the slope 11 of the reaction section 8, the air vent 14 is bored which penetrates from the upper surface of the reaction section 8 to the upper surface of the main body 30. In the example illustrated in FIGS. 1 to 3, the air vent 14 is provided in two positions at opposite corners of each short-side located end 13, i.e., four in total. The air vent may be communicated with an opening formed in a lateral surface of the main body 30.

Since the inner upper surfaces of the reaction section 8 are sloped to ascend from the center toward the short-side located ends 13 and 13 and the air vents 14 are provided at the highest positions 12 and 12 of the slopes 11 and 11, air existing in the reaction section 8 and bubbles, etc. mixed into the liquid 19 at the time of filling, which are lighter than the liquid 19, are caused to move upward along the slopes 11 defining the upper surfaces of the reaction section 8. Finally, they can be released to the outside through the air vents 14. Furthermore, since the air vents 14 extend parallel to the storage section 2 and have a height from the inner upper surface of the reaction section 8 up to the upper surface of the main body 30, the liquid 19 is allowed to flow into the air vents 14 after filling the reaction section 8, and a contact area between the liquid and air can be reduced. It is hence possible to prevent not only drying, but also unevenness in a reaction and an excessive or deficient reaction. The arrangement of the air vents 14 is not limited to the illustrated example in which two air vents are provided at each of the short-side located ends. The number of the air vents 14 may be one, or three or more for each of the short-side located ends.

The storage section 2 and the reaction section 8 are in fluid communication with each other through the communication aperture 15 provided at the center. More specifically, the communication aperture 15 is bored to penetrate from the center of the lowermost portion 6 in the inner lower surface of the storage section 2 up to the center of the inner upper surface of the reaction section 8. Since the communication aperture 15 is positioned at the center of the reaction section 8, the distance from the communication aperture 15 to the end of the reaction section 8 is shortened, and the liquid 19 can be filled to every corners of the reaction section 8 only by the force generated due to the capillary action. Furthermore, the liquid 19 stored in the storage section 2 can be caused to flow into the reaction section 8 in units of a predetermined amount through the communication aperture 15 under the combined action of the weight of the liquid 19 stored in the storage section 2, the atmospheric pressure, and the above-mentioned gradient of the inner lower surface of the storage section. Thus, any additional mechanism is not needed. It is to be noted that a speed (flow rate) at which the liquid 19 flows into the reaction section 8 from the storage section 2 can be controlled by changing the diameter and/or the length of the communication aperture 15.

The liquid filling aid 1 according to this embodiment is preferably made of a metal material having high thermal conductivity, such as stainless steel. The reason is that, by employing such a material, the liquid 19 stored in the storage section 2 can also be heated during the heating for the reaction. Conversely, when evaporation of the liquid 19 is to be suppressed or the heating is not performed, the liquid filling aid 1 may be made of a resin material having low thermal conductivity. In such a case, the reaction can be developed even with a smaller amount of the liquid 19. In addition, when the resin material is transparent, the liquid filling aid 1 can be formed such that the interior of the reaction section 8 can be visually observed.

Placement onto Slide Glass and Reaction Process

Figure 4:
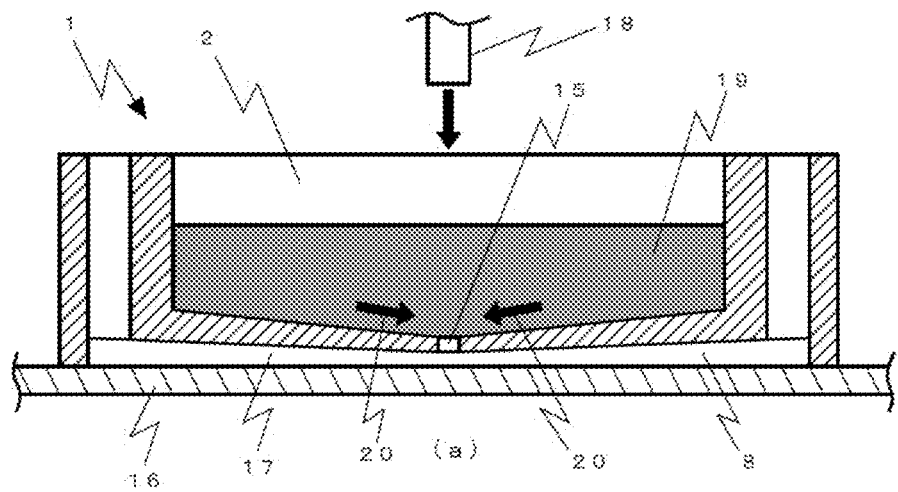
FIG. 4 is a sectional view to explain successive states of a liquid when the liquid filling aid according to the first embodiment is placed on a slide glass and the liquid is discharged. Specifically.
Figure 4:
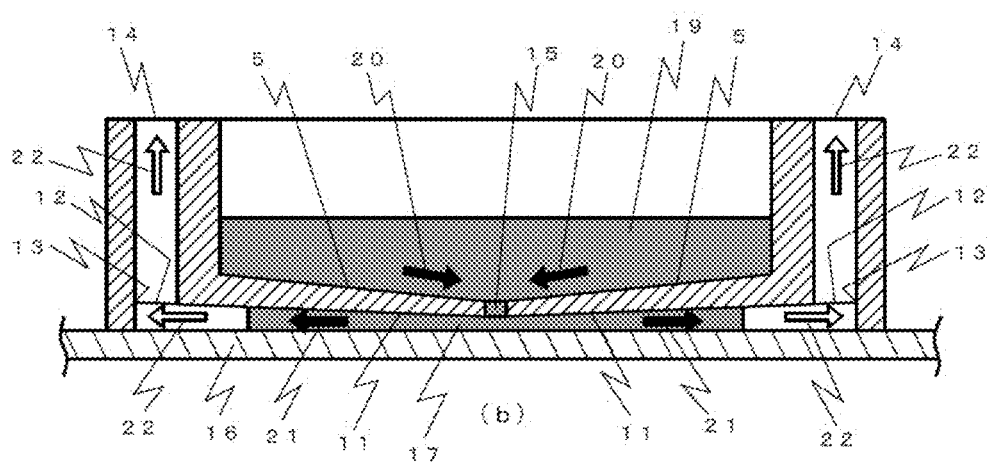
Figure 4:
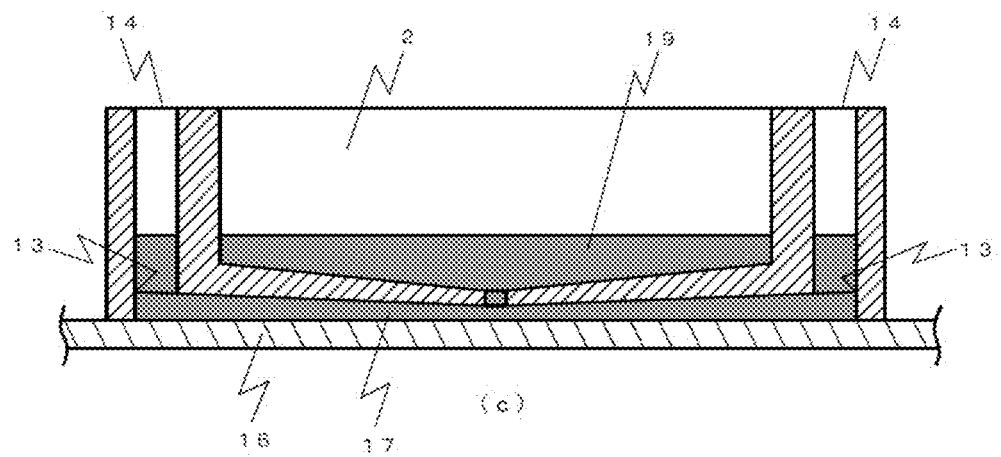

FIG. 4 is a sectional view to explain successive states of the liquid when the liquid filling aid according to the first embodiment is placed on the slide glass and the liquid is discharged. FIG. 4(a) represents a state immediately after the liquid has been discharged and supplied to the storage section, FIG. 4(b) represents a state where the liquid flows into the reaction section from the storage section through the communication aperture, and FIG. 4(c) represents a state where the liquid has been filled in the entirety of the reaction section. In the drawings, black arrows indicate flows of the liquid, and white arrows indicate flows of air.

The liquid filling aid 1 according to this embodiment is placed on the slide glass 16. Upon the placement of the liquid filling aid 1, the space defined by the reaction section 8 and the slide glass 16 forms the reaction chamber 17 in which an object substance is subjected to the reaction. The placed liquid filling aid 1 is preferably pressed downward by a holder, such as an arm. A process of filling the liquid 19 into the reaction chamber 17 and developing the reaction of the object target is executed as follows.

First, the liquid 19 is discharged from the discharge device 18 and supplied to the storage section 2 (FIG. 4(a)). At that time, the liquid 19 is discharged toward the storage section 2 once in an amount larger than the amount required for the object reaction process in excess of the volume of the reaction chamber 17. The amount of the liquid 19 supplied to the storage section 2 is preferably several to several-ten times as much as the volume of the reaction chamber 17. Here, since the opening 3 of the storage section 2 is formed over a region occupying a half or more of an area of the upper surface of the main body 30, the liquid 19 can be discharged and supplied without accurately positioning the discharge device 18.

The liquid 19 having been supplied to the storage section 2 is guided to flow along the slopes 5 at the bottom of the storage section 2 up to a position above the communication aperture 15, which is formed at the center, under the combined action of the liquid weight, the atmospheric pressure, and the gradient of the slopes 5 at the bottom of the storage section 2, and then to flow into the communication aperture 15 (as denoted by arrows 20). The liquid 19 having entered the reaction chamber 17 through the communication aperture 15 is caused to flow toward the right and left short-side located ends 13 and 13 (as denoted by arrows 21) by the force generated due to the capillary action in the space between the upper sloped surfaces 11 of the reaction chamber 17 and the slide glass 16. At that occasion, air existing in the reaction chamber 17 is caused to move along the gradient of the upper sloped surfaces 11 of the reaction chamber 17 because air is lighter than the liquid 19. Finally, the air is released to the outside through the air vents 14 formed at the highest positions 12 of the slopes (as denoted arrows 22) (FIG. 4(b)).

Since the amount of the liquid 19 stored in the storage section 2 is larger than the volume of the reaction chamber 17, the liquid 19 continues to flow into the reaction chamber 17. When the liquid 19 reaches the short-side located ends 13 and 13 of the reaction chamber 17, the liquid 19 further rises within the four air vents 14. The liquid 19 rising within the four air vents 14 is stopped at a position where the liquid 19 in the air vents 14 and the liquid 19 in the storage section 2 are balanced (FIG. 4(c)). The reason is that the storage section 2 is provided just above the reaction chamber 17 in fluid communication with it through the communication aperture 15, and that the air vents 14 penetrate from the reaction chamber 17 up to the same height as the upper end of the storage section 2 in parallel to the storage section 2. The liquid 19 rising within the air vents 14 and the liquid 19 remaining in the storage section 2 are replenished to the reaction chamber 17 without additional discharge when the amount of the liquid 19 in the reaction chamber 17 is reduced. Furthermore, since the liquid 19 rises within the air vents 14, a contact area between the liquid 19 and outside air can be reduced, and undesired drying can be prevented.

Thus, the reaction chamber 17 can be fully filled with the liquid 19 without mixing of bubbles because of the features that the gap between the reaction chamber 17 and the slide glass 16 is a sufficiently small gap to generate the force due to the capillary action over the regions spanning from the center to the short-side located ends 13 and 13 of the reaction section 8, that the upper surfaces 11 and 11 of the reaction chamber 17 are sloped, and that the plural air vents 14 are provided at the highest positions 12 of the upper sloped surfaces of the reaction chamber 17. Furthermore, the required amount of the liquid 19 can be stored and additional discharge of the liquid 19 is not needed because of the features that the storage section 2 having a larger volume than that of the reaction chamber 17 is provided just above the reaction chamber 17, and that the reaction chamber 17 and the storage section 2 are connected to each other through the communication aperture 15.

Second Embodiment

A liquid filling aid 1 according to a second embodiment is different from that according to the first embodiment mainly in including a deeply sunken portion 24. The following description is made mainly about the different point from the first embodiment, and description of common points is omitted.

Figure 8:
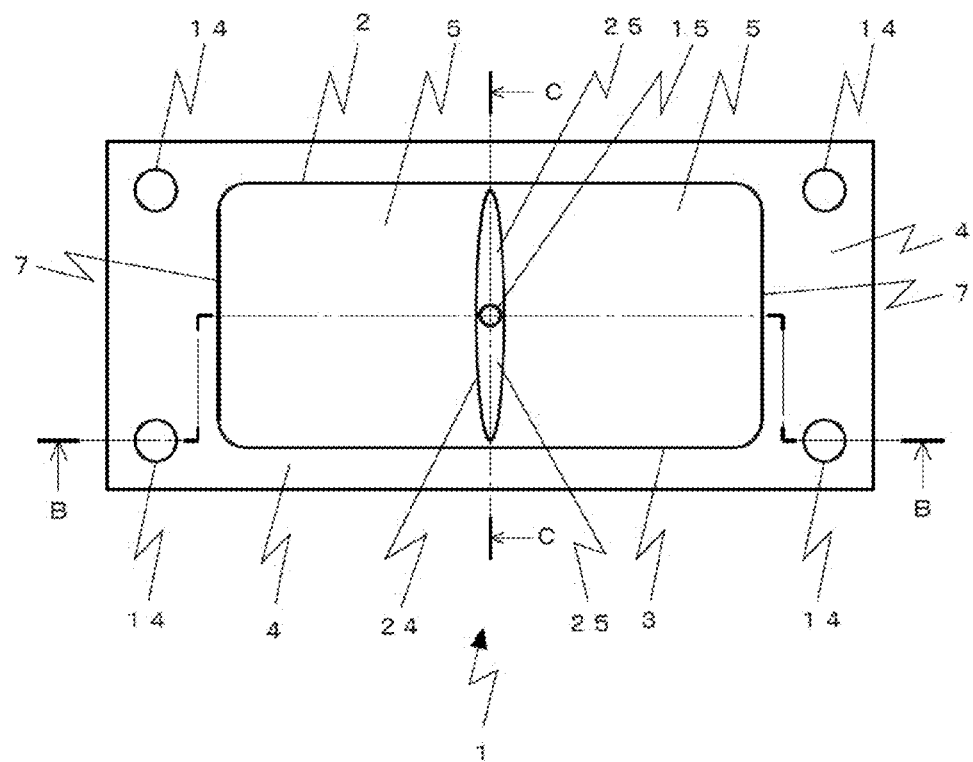
FIG. 8 is a plan view of a liquid filling aid according to a second embodiment.
Figure 9:
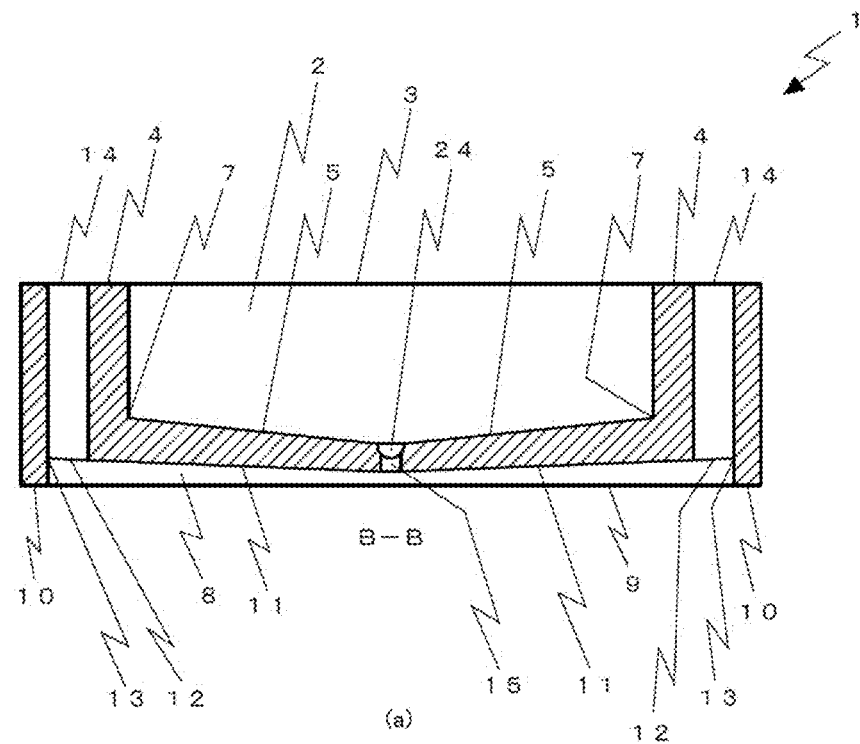
FIG. 9(a) is a sectional view taken along a line B-B in FIG. 8.
FIG. 9(b) is a sectional view taken along a line C-C in FIG. 8.
Figure 9:
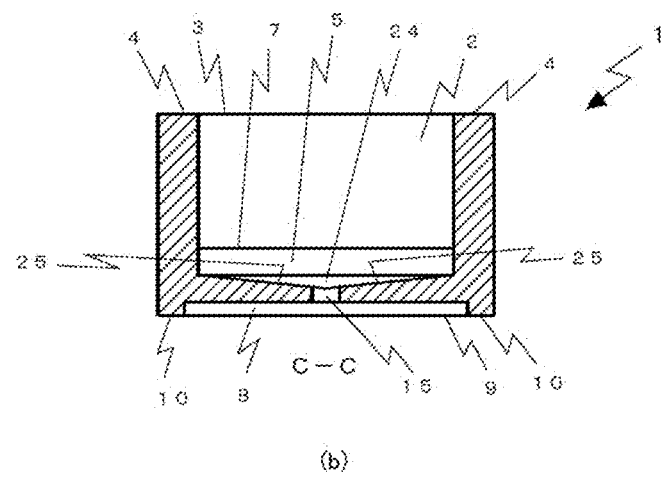

FIG. 8 is a plan view of the liquid filling aid 1 according to this embodiment, FIG. 9(a) is a sectional view taken along a line B-B in FIG. 8, and FIG. 9(b) is a sectional view taken along a line C-C in FIG. 8.

The liquid filling aid 1 according to the second embodiment is similar to that according to the first embodiment in the following points. The storage section 2, the reaction section 8, the air vent 14, and the communication aperture 15 are formed in the main body 30 made of a rectangular parallelepiped member, and the liquid filling aid 1 is placed on the slide glass 16 when it is used. However, the liquid filling aid 1 according to the second embodiment is different from that according to the first embodiment in including the deeply sunken portion 24 formed at the center of the storage section 2.

The deeply sunken portion 24 is a groove formed at the center of the storage section 2 and, when viewed from above, it has an elongate elliptic shape extending in the short-side direction of the storage section 2. The deeply sunken portion 24 has a slope 25 defining a mortar-like shape inclining toward a center, and the communication aperture 15 is provided at a center of the slope 25. Because the slope 25 is steeper than the slope 5, an amount of the liquid remaining on the slope 25 is minimal. The shapes of the deeply sunken portion 24 and the slope 25 are symmetrical relative to center lines in the vertical direction and the horizontal direction on the drawing. The shape of the deeply sunken portion 24 is not limited to the illustrated elliptic shape, and the shape of the slope 25 is not limited to the mortar-like shape.

When the deeply sunken portion 24 is called a first recess and the storage section 2 excepting the deeply sunken portion 24 is called a second recess, the deeply sunken portion 24 is constituted such that the volume of the second recess is twice or more, preferably 10 times or more, and more preferably 20 times or more as much as the volume of the first recess. In the second embodiment, the volume of the second recess (i.e., the storage section 2 excepting the deeply sunken portion 24) is 100 times or more as much as the volume of the first recess (i.e., the deeply sunken portion 24). From another point of view, the volume of the deeply sunken portion 24 is set substantially equal to or less than the volume of the reaction chamber 17, preferably equal to or less than ½ of that volume, and more preferably equal to or less than ⅓ of that volume.

The technical meaning of the presence of the deeply sunken portion 24 resides in that a minute amount (e.g., several hundred μL) of expensive liquid used in a certain step of the immunohistochemical staining method can be reliably supplied to the reaction section 8 through the communication aperture 15. An anti-human HER2/neu gene product polyclonal antibody, which is used as the primary antibody in the fourth step described in the Background Art section of this Description, is disclosed here as one example of the liquid used in a minute amount. In the step using the minute amount of liquid, the liquid in an amount ranging from substantially the same value as the volume of the deeply sunken portion 24 to a several-fold value is discharged from the discharge device toward substantially the center of the storage section 2, for supply to the storage section 2.

On the other hand, in another certain step in the immunohistochemical staining method, an inexpensive liquid is used in an amount, e.g., several ten to several hundred times as much as that of the expensive liquid. Even in that case, the liquid filling aid 1 is to be usable. In the antigen retrieval step, for example, the liquid is evaporated under heating, and hence a relatively large amount of the liquid is required. Since the liquid filling aid 1 according to this embodiment includes the second recess (i.e., the storage section 2 excepting the deeply sunken portion 24) having a larger volume than that of the first recess (i.e., the deeply sunken portion 24), the liquid filling aid 1 is adaptable for the case where the liquid is used in a relatively large amount, by employing not only the first recess, but also the second recess. An antigen retrieval solution (10 mM of sodium citrate buffer solution with pH 6.0), which is used in the third step described in the Background Art section of this Description, is disclosed here as one example of the liquid used in a relatively large amount.

With the above-described liquid filling aid 1 according to the second embodiment, the step using a minute amount of liquid and the step using a relatively large amount of liquid in the immunohistochemical staining method can be performed by employing the same liquid filling aid 1.

Details of the present invention will be described below in connection with Example, but the present invention is in no way limited by the following Example.

Example

Apparatus

Figure 5:
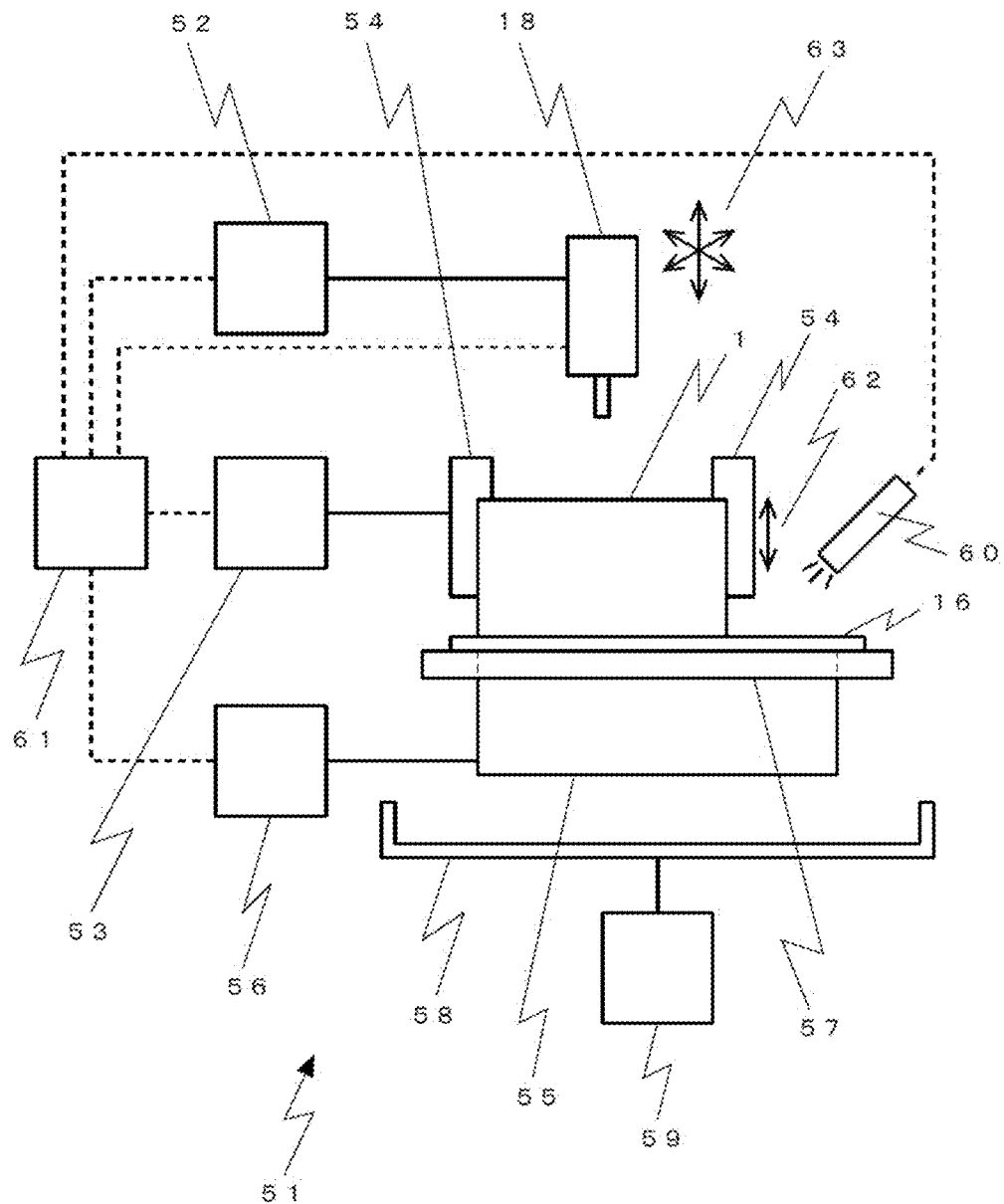
FIG. 5 is a block diagram to explain an automatic staining apparatus according to Example.

FIG. 5 is a block diagram to explain an automatic staining apparatus 51 according to Example.

The automatic staining apparatus 51 according to Example includes, as main components, a discharge device 18, a driving device 52, an elevating/lowering device 53, an arm (holder) 54, a stage 55, a heater 56, and a controller 61.

The discharge device 18 discharges the liquid 19 for developing a reaction of a biological tissue, a cell, or the like, which is bound or attached onto the slide glass 16. The discharge device 18 used in Example is a plunger type discharge device in which a liquid is discharged by moving a plunger through a desired stroke, the plunger sliding in close contact with an inner surface of a reservoir that has a nozzle at its fore end. While the plunger type discharge device is used in Example, another type of discharge device can also be of course used. Other usable discharge devices include, for example, the air type in which air under regulated pressure is applied for a desired time to the liquid in reservoir that has a nozzle at its fore end, and the tubing type in which the liquid in a flexible tube is moved by operating a plurality of rollers or key-like members to squeeze the tube. The liquid 19 is usually supplied to the discharge device 18 from a reservoir equipped in the discharge device 18. In the case using the plunger type discharge device, however, the liquid 19 may be prepared in a separate container and may be sucked from the container prior to discharging.

The discharge device 18 is mounted to the driving device 52 and is movable in XYZ directions (as denoted by arrows 63). The driving device 52 used here may be operated, for example, in combination of a ball screw and a servo motor or a stepping motor, or by a linear motor. The driving device 52 may be realized with a plurality of driving devices that are able to relatively move the discharge device 18 and the liquid filling aid 1 in the XYZ directions. For example, the driving device 52 may be realized with a first driving device disposed on the side including the arm 54 for movement in the X or Y direction, and a second driving device disposed on the side including the discharge device 18 for movement in the X or Y direction and the Z direction.

The automatic staining apparatus 51 according to Example includes the elevating/lowering device 53 to place and fix the liquid filling aid 1 according to the embodiment onto the slide glass 16. The liquid filling aid 1 is grasped by the arm 54 mounted to the elevating/lowering device 53 and is vertically moved between an elevated position where the liquid filling aid 1 is away from the stage 55, and a lowered position where the liquid filling aid 1 is held in contact with the stage 55 with the slide glass 16 interposed therebetween (as denoted by arrows 62). The elevating/lowering device 53 used here may be of the same type as the driving device 52, or of the type using an air cylinder, for example. The arm 54 may include a rotating shaft used to incline the liquid filling aid 1 in the grasped state such that the liquid 19 is drained out.

The automatic staining apparatus 51 further includes, under the slide glass 16, a frame-shaped palette 57 that holds the slide glass 16, and the stage 55 that is positioned within an opening formed at a center of the palette 57, and that supports the slide glass 16 in a downward pressed state. A groove having a size substantially equal to or slightly larger than that of the slide glass 16 is recessed in an upper surface of the palette 57 to facilitate positioning of the slide glass 16 when it is placed on the palette 57. As an alternative, a projection with a height not exceeding the thickness of the slide glass 16 may be provided on the upper surface of the palette 57 in surrounding relation to the slide glass 16. The stage 55 includes the heater 56 such that the slide glass 16 in contact with the stage 55 can be heated. Under the stage 55, there are disposed a liquid receiver 58 and a tank 59, the tank 59 accommodating various liquids received by the liquid receiver 58. The liquid receiver 58 is used to recover a washing liquid after the end of washing in a later-described washing step, the liquid 19 after the end of the reaction, and so on.

Figure 6:
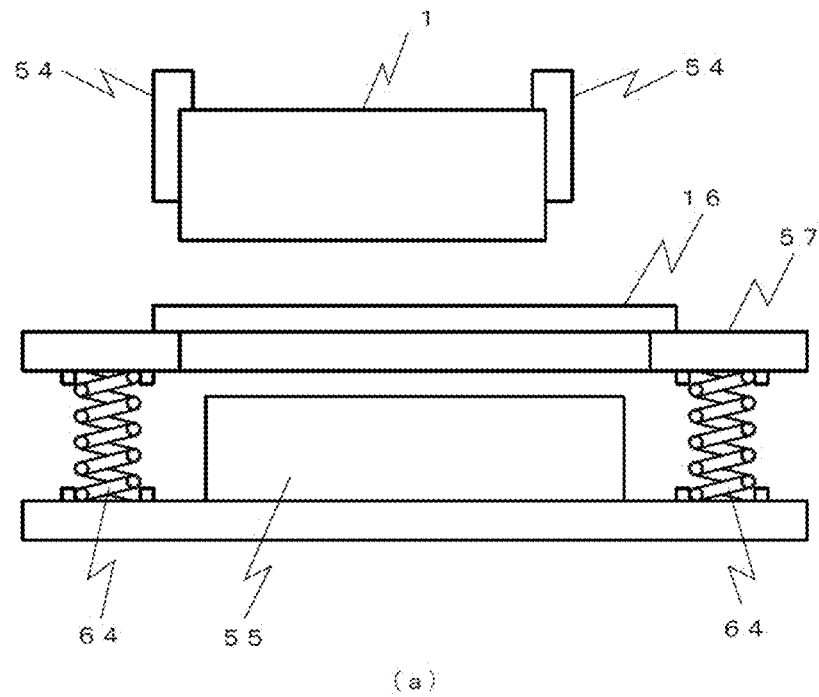
FIG. 6 is an explanatory view to explain the relation between a stage and a palette in the automatic staining apparatus according to Example. Specifically.
Figure 6:
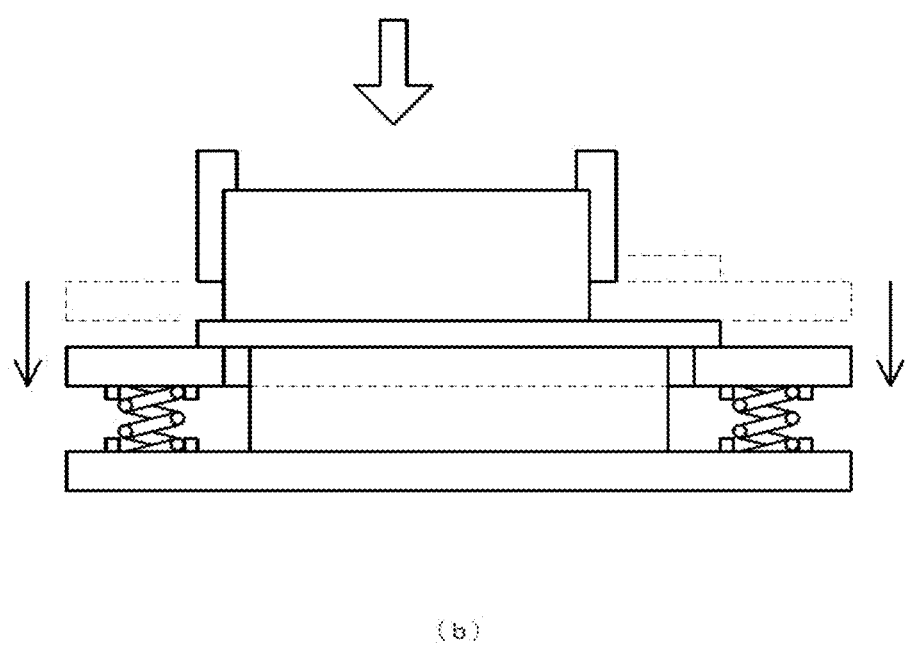

The palette 57 and the stage 55 are related to each other as follows. The palette 57 is supported at its lower surface by springs 64. Before the liquid filling aid 1 is placed, a surface (upper surface) of the palette 57 on which the slide glass 16 is held is positioned above a surface (upper surface) of the stage 55 by which the slide glass 16 is to be supported (FIG. 6(*a*)). When the slide glass 16 is put on the palette 57 and the liquid filling aid 1 is placed thereon and pressed downward, the springs 64 supporting the palette 57 are contracted, and a lower surface of the slide glass 16 is brought into contact with the upper surface of the stage 55 that is positioned within the opening of the palette 57, whereby the slide glass 16 is fixedly sandwiched between the liquid filling aid 1 and the stage 55 (FIG. 6(*b*)). Thus, the slide glass 16 and the liquid filling aid 1 are fixed without leaving gaps between them under combination of a pressing force acting downward by the elevating/lowering device 53 and biasing forces acting upward by the springs 64. As a result, the reaction chamber 17 being less susceptible to leakage can be formed without providing a sealing member, a packing, or the like. Moreover, since the slide glass 16 is firmly fixed to the stage 55 as well, heat can be efficiently conducted to the slide glass 16 when the heater 56 is used.

The automatic staining apparatus 51 according to Example further includes an air blower 60 to remove dust, the washing liquid, and so on, which are attached to the slide glass 16. The air blower 60 is constituted, for example, as a device in which a nozzle is connected to a pressurized air source for spraying compressed air, and in which supply and stop of the compressed air is switched over with operation of a solenoid valve, for example. The air blower may have some other configuration insofar as the compressed air can be selectively sprayed.

The above-mentioned components are controlled by the controller 61. The controller 61 is constituted mainly by an input/output device, a storage device, and a processing device. For example, a personal computer, a programmable controller, or the like can be used as the controller 61.

Operation

Figure 7:
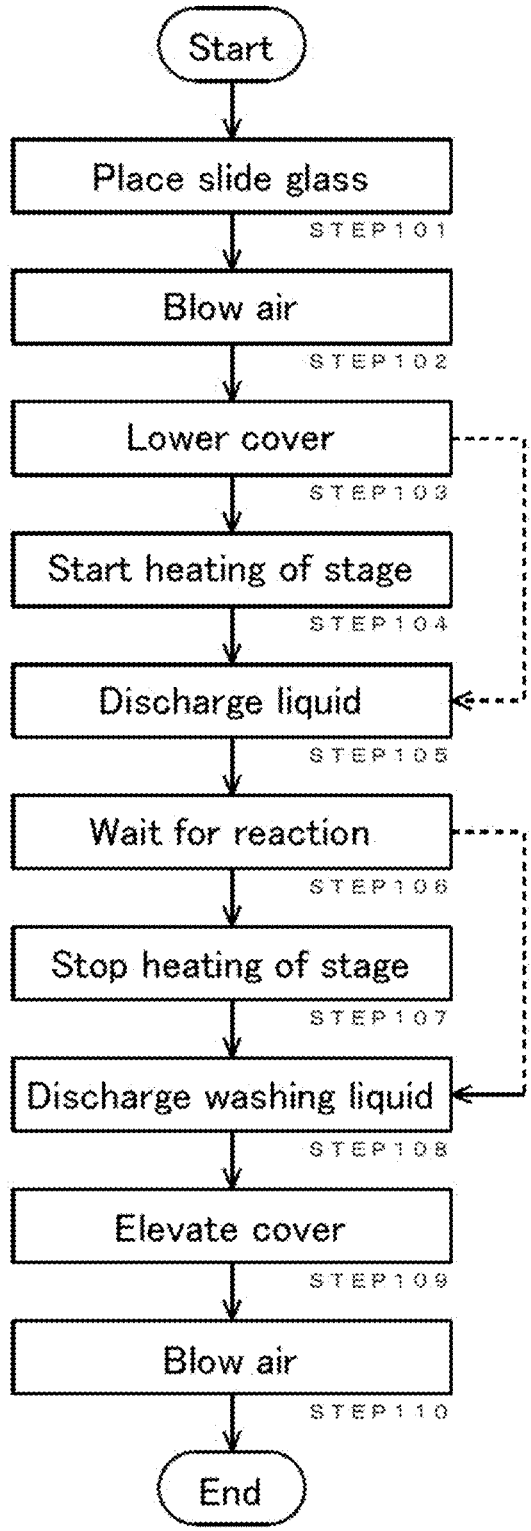
FIG. 7 is a flowchart to explain an example of operation of the automatic staining apparatus according to Example.

FIG. 7 is a flowchart to explain an example of operation of the automatic staining apparatus according to Example.

The following operation of the automatic staining apparatus represents, by way of example, operation in one typical process (corresponding to the second and third steps described above) among the plural steps constituting the above-described operations for the immunohistochemical staining method. However, details of the operation may be slightly different in several points, such as the presence or the absence of heating of the stage, the presence or the absence of elevating and lowering movements of the liquid filling aid, and a reaction waiting time, depending on the types of the steps.

Initially, the slide glass 16 to which the object substance is bound is placed on the palette 57 (STEP 101). Then, air is blown to remove dust, the washing liquid, and so on, which are attached to the slide glass 16 (STEP 102). After the end of the air blowing, the liquid filling aid 1 is lowered by the elevating/lowering device 53, and the slide glass 16 is fixed in a state sandwiched between the liquid filling aid 1 and the stage 55 (STEP 103). After fixing the slide glass 16, heating of the stage 55 is started when the heating is needed (STEP 104). When the heating is not needed, the processing flow is advanced to a next step without executing STEP 104. The liquid 19 is then discharged toward the storage section 2 in the upper portion of the liquid filling aid 1 (STEP 105). The liquid 19 supplied to the storage section 2 in the upper portion of the liquid filling aid 1 flows into the reaction section 8 through the communication aperture 15, and it is filled in the reaction chamber 17 defined by the slide glass 16 and the reaction section 8 as described above. The liquid 19 reacts with the object substance that is previously bound to the slide glass 16. The apparatus is held in a state waiting for the lapse of a predetermined time such that the reaction is sufficiently developed (STEP 106). The predetermined time is different depending on the types of the object substance and the liquid. After the lapse of the predetermined time, the heating of the stage 55 is ended (STEP 107) when the heating has been performed. When the heating has not been performed, the processing flow is advanced to a next step without executing STEP 107. Then, the washing liquid is discharged in the same state as in the preceding step without elevating the liquid filling aid 1 and is filled into the reaction chamber 17 as in the case of filling the liquid 19 (STEP 108). After the end of the washing step, the liquid filling aid 1 is elevated and the washing liquid is drained out (STEP 109). The drained washing liquid is recovered into the liquid receiver 58 and is stored in the tank 59. Then, air is blown to remove the washing liquid, etc. remaining on the slide glass 16 (STEP 110). The foregoing is the operation of one typical process.

When another process is to be executed subsequently, it is basically just required to repeat the above-described steps. However, the step of placing the slide glass 16 on the palette 57 (STEP 101) and one of the air blowing steps (STEP 102 or STEP 110) may be omitted.

As described above, since the liquid filling aid includes, just above the reaction section, the storage section having a larger volume than that of the reaction section, additional discharge of the liquid is not needed, and the number of steps can be reduced. Furthermore, since the liquid is stored in the storage section, the liquid necessary for the reaction is not exhausted even when the liquid is evaporated during the step in which heating is performed. Accordingly, unevenness in a reaction and an excessive or deficient reaction will not occur.

REFERENCE SIGNS LIST

1: liquid filling aid, 2: storage section, 3: opening (storage section), 4: wall (storage section), 5: slope (storage section), 6: lowermost portion, 7: short-side located end (storage section), 8: reaction section, 9: opening (reaction section), 10: wall (reaction section), 11: slope (reaction section), 12: highest position, 13: short-side located end (reaction section), 14: air vent, 15: communication aperture, 16: slide glass, 17: reaction chamber, 18: discharge device, 19: liquid, 20, 21: flows of liquid, 22: flow of air, 24: deeply sunken portion, 25: slope, 30: main body, 51: automatic staining apparatus, 52: driving device, 53: elevating/lowering device, 54: arm (holder), 55: stage, 56: heater, 57: palette, 58: liquid receiver, 59: tank, 60: air blower, 61: controller, 62: elevating and lowering direction (up and down direction) of liquid filling aid, 63: moving directions (XYZ directions) of discharge device, 64: spring

The invention claimed is:

1. A liquid filling aid that is placed on a plate-shaped member and defines a reaction chamber to be filled with a liquid, the aid comprising:
   a main body;
   a storage section that is formed in the main body and stores the liquid;
   a reaction section that is a recess formed at a bottom of the main body;
   a communication aperture extending between the storage section and the reaction section;
   a lower surface of said storage section being configured such that liquid stored in the storage section flows down into the reaction section through the communication aperture; and
   an air vent for communication between the reaction section and outside air,
   wherein the reaction section and an upper surface of the plate-shaped member define the reaction chamber,
   wherein the storage section and the reaction section are constantly communicated by the communication aperture, and
   wherein an inner upper ceiling surface of the reaction section has a gradient ascending toward the air vent.

2. The liquid filling aid according to claim 1, wherein the storage section has a larger volume than the reaction section.

3. The liquid filling aid according to claim 1, wherein the storage section is arranged directly above the reaction section with the communication aperture interposed therebetween.

4. The liquid filling aid according to claim 3, wherein an opening of the storage section is formed in an upper surface of the main body.

5. The liquid filling aid according to claim 1, wherein the air vent penetrates from an upper surface of the reaction section up to an upper surface of the main body.

6. The liquid filling aid according to claim 1, wherein the reaction section is constituted with a depth at which a force due to capillary action is generated over an entire region of the reaction section.

7. The liquid filling aid according to claim 6, wherein the depth of the reaction section is 10 to 200 µm.

8. The liquid filling aid according to claim 1, wherein the storage section includes a first recess in which the communication aperture is provided, and a second recess that is positioned above the first recess, and that has a volume twice or more as much as that of the first recess.

9. The liquid filling aid according to claim 1, wherein the main body is made of a metal material.

10. The liquid filling aid according to claim 1, wherein the plate-shaped member is a slide glass used in a staining step.

11. An automatic staining apparatus comprising:
a liquid discharge device;
a palette that holds a slide glass;
a driving device that moves the discharge device in XYZ directions relative to the palette;
a holder that holds the liquid filling aid according to claim 10; and
an elevating/lowering device that moves the holder up and down.

12. A liquid filling method using the liquid filling aid according to claim 1, the method comprising:
a step of placing the liquid filling aid on the plate-shaped member; and
a step of discharging the liquid in an amount equal to or larger than the volume of the reaction chamber to the storage section.

13. The liquid filling aid according to claim 1, wherein the communication aperture extends between the storage section and substantially a center of the reaction section.

14. The liquid filling aid according to claim 1, wherein the air vent is constituted as a plurality of air vents that are disposed with the aperture interposed therebetween.

15. The liquid filling aid according to claim 14, wherein the aperture is constituted as a single aperture.

16. The liquid filling aid according to claim 15, wherein an opening of the storage section is formed over a region occupying a half or more of an area of the upper surface of the main body.

17. The liquid filling aid according to claim 14, wherein an opening of the storage section is formed over a region occupying a half or more of an area of the upper surface of the main body.

18. The liquid filling aid according to claim 1, the reaction section and the outside air are constantly communicated by the air vent.

* * * * *